United States Patent [19]

Leonard et al.

[11] Patent Number: 4,873,266

[45] Date of Patent: Oct. 10, 1989

[54] MENTHONE ENHANCEMENT OF TRANSDERMAL DRUG DELIVERY

[75] Inventors: Thomas W. Leonard; Karol Kay Mikula, both of Clinton, N.Y.; Marcia S. Schlesinger, Middlesex, N.J.

[73] Assignee: American Home Products Corp., New York, N.Y.

[21] Appl. No.: 3,977

[22] Filed: Jan. 16, 1987

[51] Int. Cl.$^4$ .................... A61K 31/12; A61K 31/135
[52] U.S. Cl. ..................................... 514/653; 514/690
[58] Field of Search ................................ 514/653, 690

[56] References Cited

U.S. PATENT DOCUMENTS

| | | |
|---|---|---|
| 3,551,554 | 12/1970 | Herchler ................................ 424/7 |
| 3,896,238 | 7/1975 | Smith .................................. 424/358 |
| 3,952,099 | 4/1976 | Smith .................................. 424/227 |
| 3,989,816 | 11/1976 | Rajadhyaksha ...................... 424/60 |
| 4,046,886 | 9/1977 | Smith .................................. 424/227 |
| 4,316,893 | 11/1976 | Rajadhyaksha ...................... 424/60 |
| 4,405,616 | 9/1983 | Rajadhyaksha ..................... 424/244 |

Primary Examiner—Stanley J. Friedman
Attorney, Agent, or Firm—Adley F. Mandel

[57] ABSTRACT

Disclosed herein are compositions and methods for enhancing the transdermal delivery of physiologically active agents across mammalian skin or membranes and which comprise a percutaneous transfer enhancing amount of l-menthone and a drug.

2 Claims, No Drawings

MENTHONE ENHANCEMENT OF TRANSDERMAL DRUG DELIVERY

BACKGROUND OF THE INVENTION

This invention relates to the transdermal delivery of physiologically active agents and more particularly to the enhancement of the transfer of such agents percutaneously by incorporation into the transdermal delivery system of a small amount of 1-menthone.

The development of new or improved dosage forms and delivery means for physiologically active agents has been and will continue to be the subject of research for both existing and novel drugs. In too many instances a particular drug dosage provides for more drug than is actually required to produce an efficacious and safe therapeutic blood level free from said effects. The reasons for such theoretically excessive doses are many and include, inter alia, the mode of administration, the metabolism of the drug in the gastrointestinal tract, the absolute absorbtion (bioavailability) of the drugs and the situs of absorption. In another aspect the use of sustained release dosage forms and delivery means has increased to further both patient compliance and convenience.

More recently, investigations respecting transdermal drug delivery systems have increased resulting in a number of commercially available products especially for the administration of nitroglycerine. These later systems apparently provide the advantages inherent is sustained delivery dosage forms and avoid the problems of a drug's rapid metabolism upon oral administration. At the same time less drug, although equally efficacious therapeutically to a greater amount orally administered, is ingested or absorbed by the patient. Nevertheless, the feasibility, the success and potential of such transdermal systems have heretofore been limited to drugs that are efficacious at lower dose levels and/or have relatively limited water solubility. The explanation for such limitations arise for the formidable barrier provided by the external layer(s) of animal skin and membrane tissues and the limited body areas which are usefully available for application of such transdermal dosage forms.

Various efforts have been pursued to expand the availability of transdermal delivery to more drugs and overcome the barrier presented by animal skin and membrane. Most such efforts, at least those employing transdermal drug delivery devices, have concentrated on increasing the diffusion of the drug from the device into and through the aforementioned barriers. Other efforts have been more specifically targeted at improving the permeability characteristics or percutaneous absorption capacity of the barrier itself. While some of these latter efforts have reportedly shown some success, the agents employed frequently have caused undesirable systemic side effects as well as tissue damage and irritation at the stius of application.

Agents reported to act as penetration enhancers for transdermal drug delivery include dimethylsulfoxide, disclosed in U.S. Pat. No. 3,551,554; combinations of sucrose fatty acid esters with a sulfoxide or phosphoric oxide, disclosed in U.S. Pat. Nos. 3,896,238; 3,952,099 and 4,046,886; and the 1-substituted azacycloalkan-2-ones which are the subject of U.S. Pat. Nos. 3,989,816; 4,316,893 and 4,405,616.

SUMMARY OF THE INVENTION

The present invention relates to compositions useful for the transdermal delivery of physiologically active agents to mammals. More particularly, this invention relates to compositions and methods which enhance the percutaneous transfer of topically applied, systemically active drugs and particularly such drugs which have aqueous solubility or which can be made water soluble by the use of derivatives, or in composition, through selection of appropriate pH, buffers, solvents and excipients. Thus the composition of this invention comprises at least one systemically active, water soluble or solubilizable drug, a percutaneous transfer enhancing amount of 1-menthone and a pharmaceutically acceptable vehicle in which the 1-menthone is soluble.

The structure formula for 1-menthone is:

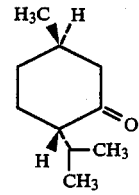

In a further aspect, the invention relates to a method for enhancing the transfer of physiologically active agents into and through mammalian skin and membranes. The method comprises topically applying or administering to substantially the same section of the mammalian skin or membrane an effective amount of a systemically active, water soluble or solubilizable drug, a percutaneous transfer enhancing amount of 1-menthone or a pharmaceutically acceptable vehicle.

Still a further embodiment of this invention resides in a unit dosage form for transdermal delivery of physiologically active agents to mammals. The dosage form comprises an effective amount of a systemically active, water soluble or solubilizable drug comprised within at least one drug reservoir means; a percutaneous transfer enhancing amount of 1-menthone comprised within 1-menthone delivery means; 1-menthone solubilizing means and securing means for attaching the dosage form to a mammal.

DETAILED DESCRIPTION OF THE INVENTION 1-menthone can be obtained naturally from peppermint or other oils or prepared synthetically. It has now been found that 1-menthone acts to enhance the percutaneous transfer of systemically active drugs in mammal.

Thus, this invention provides a topical composition for the transdermal delivery of physiologically active agents to mammals, said composition comprising an effective amount of a systemically active, water soluble or solubilizable drug, a percutaneous transfer enhancing amount of 1-menthone and a pharmaceutically acceptable vehicle comprising at least one pharmaceutically acceptable solvent or solubilizer for said 1-menthone.

In this invention the effective amount of drug will mean that amount of drug needed to produce a therapeutic dose following its transdermal administration. That amount will vary, depending, among other factors, on the physiological effect desired, the frequency of administration, drug and intradermal metabolism, drug half-life and the amount of 1-menthone and perhaps other percutaneous transfer enhancers employed in the composition.

As stated, a percutaneous transfer enhancing amount of 1-menthone is comprised in the comosition. This amount for most drugs, generally ranges from about 4 to about 16 percent by weight of the composition.

The composition of the invention will further include a pharmaceutically acceptable vehicle containing at least one pharmaceutically acceptable solvent or solubilizer for said 1-menthone. The vehicle in preferred compositions will also contain at least one pharmaceutically acceptable solvent which is a solvent or solubilizer for the drug. The respective solvents or solubilizers for the drug and 1-menthone of this invention may be the same or different. In either case it is preferable that the solvents or solubilizers for each the drug and 1-menthone, in the amounts employed, are at least partially soluble or miscible with each other. Most preferably, the solvents or solubilizers for each the drug and the 1-menthone will, in the amounts employed, be wholly soluble or miscible with each other. The pharmaceutically acceptable vehicle may also contain other pharmaceutically acceptable excipients useful for formulating topical pharmaceutical compositions including buffers, neutralizing agents, pH modifiers, viscosity building or controlling agents, gel forming agents, emulsifiers, surfactants, polymers and the like.

Examples of solvents or solubilizers which may comprise the pharmaceutically accepable vehicle of this invention include one or more of materials such as glycerin, propylene glycol, isopropanol, ethanol, a variety of polyethylene glycols, block copolymers or ethylene glycol and propylene glycol, acetylated monoglycerides, lanolin, mineral oil, water, aqueous buffers and the like.

The composition of this invention for application to mammalian skin or membrane may take various forms including creams, lotions, gels, ointments, suppositories, sprays, aerosols and the like.

In another embodiment, the invention includes a method for treating mammals in need of treatment with systemically active agents by the transdermal administration of said agents sequentially or in combination with a percutaneous transfer enhancing amount of 1-menthone. The method is effected by topically administering to substantially the same section of mammalian skin or membrane an effective amount of a systemically active, water soluble or solubilizable drug, a percutaneous transfer enhancing amount of 1-menthone and a pharmaceutically acceptable vehicle. Thus, the method of the invention may also be employed as referred to hereinabove in the Summary of the Invention as a method for enhancing the transfer of physiologically active agents through mammalian skin and membranes. In either event the method may be realized through administration of the composition of the invention, a unit transdermal dosage form comprising the composition of the invention, or through sequential administration of the percutaneous transfer agent and drug of this invention via direct application to said mammal or via the unit transdermal dosage form of this invention comprising the same or different means for delivery of each of said percutaneous transfer agent and said drug.

The unit dosage form of this invention as hereinbefore described comprises an effective amount of a systemically active water soluble or solubilizable drug comprised within at least one drug reservoir means. Said drug reservoir means may take various forms such as pads or sponges impregnated with drug, a polymeric matrix containing the drug or composition of the drug, a gel formulation (or other formulation having some structural integrity) of the drug, a composition or solution of the drug within a walled container permeable to the drug and available to the skin or membrane of the mammal, a multiplicity of distinct microreservoir compartments containing the drug or drug composition within or homogenously throughout each microreservoir, layers of reservoirs and multiple variants of any of these enumerated and other drug reservoir presentations.

The unit dosage form, as with the other embodiments of this invention, further comprises a percutaneous transfer enhancing amount of 1-menthone. In the unit dosage form, the 1-menthone will be comprised within 1-menthone delivery means which means can be selected from any of the described drug reservoir means, distinct 1-menthone reservoir means and integral 1-menthone reservoir means. Integral 1-menthone reservoir means is defined to include the provision of the 1-menthone together with the securing means, as for example in an adhesive layer.

1-Menthone solubilizing means and securing means for attaching or maintaining contact of the dosage form to a mammal are also comprised by the unit dosage form of the invention. The 1-menthone solubilizing means comprise a pharmaceutically acceptable vehicle in which the 1-menthone is soluble or solubilizable and which further is also either a solvent for the drug or is miscible with the drug or drug composition. Thus the 1-menthone solubilizing means may be formulated with any of the 1-menthone, the drug and/or in a distinct reservoir or depot within the unit dosage of the invention, so long as the 1-menthone is soluble or made soluble therein and the drug or drug composition is soluble or miscible therewith prior to transfer through the skin or membrane of the mammal. The securing means will be selected from adhesives, belts such as those with "velcro" fittings, elastic bands or such other devices which are capable of securely attaching the unit dosage to the mammalian subject.

The invention is further illustrated by the following examples.

The examples given below are the results of in vitro diffusion cell experiments performed on freshly excised nude mouse skin. A piece of freshly excised nude mouse skin was mounted across the 0.79 cm$^2$ opening of a diffusion cell. Between 10 and 20 mg of test formulation was impregnated into 0.79 cm$^2$ disks of non-woven rayon fabric and these impregnated circles were applied to the epidermal side of the skin. The dermal side of the skin was in contact with pH 7.4 buffer solution maintained at 32° C. for 24 hours. The receiving fluid was periodically sampled and assayed for drug content. For albuterol formulations, the analyses were conducted by HPLC. Formulations for the drug were prepared in one solvent system and varying amounts of 1-menthone, were added systematically. The total percent of drug diffused through the skin was determined and this vlaue was compared to an unenhanced formulation of the drug in the solvent system. The results are presented in the following examples and show conclusively that 1-menthone, facilitates percutaneous diffusion of drugs.

EXAMPLE 1

Percutaneous Diffusion of Albuterol through Nude Mouse Skin from 1-Menthone Enhanced Formulations

| Formulation # | Formulation (w/w %) | | | Total Percent Drug Diffused in 24 Hours |
|---|---|---|---|---|
| | Albuterol | Sol-vent** | 1-menthone | |
| A1 | 5 | 95 | 0 | 33.9 |
| A5 | 5 | 90 | 5 | 68.8 |
| A6 | 5 | 85 | 10 | 88.7 |
| A7 | 5 | 80 | 15 | 87.6 |

**Sovent = 33% N—methyl-2-pyrrolidone
67% Diethylene glycol monoethyl ether

What is claimed is:

1. A topical composition for the transdermal delivery of physiologically active agents to mammals by topical administration comprising an effective amount of a systemically active, water soluble or solubilizable drug, a percutaneous transfer enhancing amount of 1-menthone and a pharmaceutically acceptable vehicle comprising at least one pharmaceutically acceptable solvent or solubilizer for said 1-menthone, wherein said water soluble or solubilizable drug is albuterol.

2. A method for enhancing the transfer of physiologically active agents through mammalian skin and membranes comprising topically administering to substantially the same section of mammalian skin or membrane an effective amount of systemically active, water soluble or solubilizable drug, a percutaneous transfer enhancing amount of 1-menthone and a pharmaceutically acceptable vehicle, wherein said water soluble or solubilizable drug is albuterol.

* * * * *